United States Patent
Relihan et al.

(10) Patent No.: US 6,233,310 B1
(45) Date of Patent: May 15, 2001

(54) EXPOSURE MANAGEMENT AND CONTROL SYSTEM AND METHOD

(75) Inventors: Gary F. Relihan, Nashotah; Clarence L. Gordon, III, Delafield, both of WI (US); George C. Goodman, Niskayuna, NY (US); Baoming Ma, Cherry Hill, NJ (US)

(73) Assignee: General Electric Company, Milwaukee, WI (US)

( * ) Notice: Subject to any disclaimer, the term of this patent is extended or adjusted under 35 U.S.C. 154(b) by 0 days (21) Appl. No.: 09/351,755

(22) Filed: Jul. 12, 1999

(51) Int. Cl.$^7$ ..................................... H05G 1/44
(52) U.S. Cl. ........................... 378/108; 378/110
(58) Field of Search ............................ 378/101, 108–112

(56) References Cited

U.S. PATENT DOCUMENTS 5,680,430 * 10/1997 Khutoryansky ..................... 378/109
5,867,555 * 2/1999 Popescu et al. ...................... 378/16

OTHER PUBLICATIONS

Co–pending, commonly assigned U.S. Serial No. 09/351,469, entitled Image Quality Optimization Using An X–Ray Spectra Model Based Optimization, filed Jul. 12, 1999.

* cited by examiner

Primary Examiner—David V. Bruce
(74) Attorney, Agent, or Firm—Barbara Joan Haushalter; Christian G. Cabou; Phyllis Y. Price (57) ABSTRACT

An exposure management and control system and method for x-ray technique selection is provided. Optimal x-ray technique, which affects image quality, can be accurately predetermined to use for any application. A patient model is combined with a closed loop brightness control, using a parameter that does not affect image quality. This is used to create a control system that operates as a knowledge based control system. The x-ray system brightness control system comprises a first and second regulator. The first regulator is an image quality, or brightness, regulator. The brightness regulator can have multiple functions, such as peak mA control, power limiter, skin dose limiter, and an override function. The second regulator is a dose error regulator. The second regulator is independent of the first regulator, and cooperates with the first regulator to provide x-ray technique optimization independent of brightness control.

18 Claims, 5 Drawing Sheets

EXPOSURE MANAGEMENT AND CONTROL SYSTEM AND METHOD

TECHNICAL FIELD

The present invention relates to the use of automatic x-ray technique control in fluoroscopic and record x-ray acquisition modes.

BACKGROUND ART

The function of fluoroscopy is to provide a real time imaging mode for various x-ray procedures. Some procedures use the fluoroscopic mode as a means of positioning the recording device through visualization of the internal anatomy of a patient. The recording device will then be presented with the same view as in the fluoro mode, resulting in properly framed images suitable for diagnosis. This type of procedure generally requires a minimal amount of fluoroscopic time, generally less than five minutes. Other procedures use the fluoroscopic mode as the primary mode for positioning instruments within the body, conducting medical intervention, and performing a medical diagnosis of a patient based on the fluoroscopic images. These procedures can be very lengthy and require a lengthy exposure to the x-ray radiation, as long as 2 hours or more.

The optimal x-ray technique used for each of these procedures varies with the type of medical exam being performed and the objective of the exam. For example, vascular procedures typically require kVp settings in the 70 to 90 kVp range for imaging iodinated vessels, whereas gastrointestinal (GI) studies, on the other hand, prefer higher kVp for penetrating barium contrast media. In addition, the technique may also vary as a function of the patient size.

Therefore, a x-ray technique control system that is faced with this multitude of operating situations is preferably designed to accommodate as many of the clinical imaging requirements as possible. The resulting control system then requires knowledge of many aspects of the procedure and patient in order to provide the optimal techniques for each situation.

There are several parameters, or techniques, which are to be controlled in order to effectively accomplish the tasks just outlined. These include kVp, mA, pulse width (exposure time), image quantum noise level (i.e., image receptor entrance exposure or entrance exposure rate). These also include focal spot, x-ray beam spectral quality and patient entrance radiation exposure rate (or Air Kerma). Each of these parameters has an optimal setting, which is unique for each of the procedure demands and patient sizes encountered.

Present control schemes depend on the control of brightness as the mechanism for controlling technique settings. Various methods, usually controlling a single parameter at a time, or having several independent brightness loops, are used to set the technique. Alternate algorithms, which provide better Image Quality control, might be used to allow for several variations in technique trends in controlling brightness but usually a single control parameter dominates the control action.

It would be desirable to have a brightness control system which controls and provides optimal techniques for any clinical application.

SUMMARY OF THE INVENTION

An exposure management and control system and method for x-ray technique selection is provided. Optimal x-ray technique, which affects image quality, can be accurately predetermined to use for any application. A patient model is combined with a closed loop brightness control, using a parameter that does not affect image quality. This is used to create a control system that operates as a knowledge based control system.

A x-ray system brightness control system controls brightness and provides optimal techniques for any clinical application. The brightness control system comprises a first and second regulator. The first regulator is a dose, or brightness, regulator. The brightness regulator has four functions, including peak mA control, power limiter, skin dose limiter, and an override function. The second regulator is an image quality regulator. The second regulator cooperates independently with the first regulator to provide x-ray technique optimization independent of brightness control.

Accordingly, the present invention provides brightness regulation and image quality regulation. The brightness control system can therefore achieve optimal image quality for fluoroscopy or radioscopy applications.

DETAILED DESCRIPTION OF THE PREFERRED EMBODIMENTS

The development of the exposure management and control system is preferably a model-based design. The concept allows for accurate pre-determination of the optimal x-ray technique, which affects image quality, to use for any application. By combining the knowledge of a patient model with a closed loop brightness control, a hybrid control system is created which operates as a knowledge based control system. The closed loop brightness control uses a parameter that does not affect image quality. The closed loop operation removes uncertainty present in the model.

Model parameters which affect image quality include kVp, pulse width, image receptor entrance exposure or exposure rate, and focal spot. Parameters used to control the x-ray beam spectral quality also affect image quality. All of these parameters are used by the control system, and can be stored in a table. The table can be indexed by relative patient size or by absorption. Relative patient size implies x-ray absorption, rather than physical size. The x-ray tube current, mA, is also present in these tables as a reference value. This reference value can be used as a default if no patient absorption data is available to the function.

Tube current, which is not a direct contributor to image quality, is affected by changes in x-ray beam collimation and source-to-image distance (SID). Those parameters are not related to patient size. This is significant in that control systems which do not use mA exclusively as the dose control parameter vary other parameters. These parameters include contrast, resolution, and/or signal-to-noise ratio. These parameters are varied as a function of collimation, field of view or source-to-image distance. A separate loop in this design allows for tube current to vary independently as these system situations occur without changing the techniques that control image quality. Some systems use mAkVp couples as a control system. Such systems are an example of a design which affects, and possibly degrades, image quality to satisfy entrance dose needs.

Separate tables, or image quality trajectories, are created for each application/medical procedure which requires a different set of techniques. Exams imaging iodine contrast media versus exams imaging barium contrast media require different techniques for the same relative patient size. There is one complete set of techniques versus relative patient size for each unique set of imaging requirements. Hence, there is a need for several of these trajectories.

The image quality trajectories can be developed using any suitable method. Computer modeling tools and applications experience, as related to proper x-ray techniques that are clinically acceptable can be used. A priori computer modeling, real-time computer modeling, and manual generation can also be used. Contrast, noise, and the ability to image small objects such as guide wires and stints can be specifically considered. These parameter+s are used when developing the trajectories for a specific clinical application. Also, x-ray tube/generator limitations are included in the development.

Furthermore, the x-ray system does not have infinite power capabilities. Nor can it use excessive radiation to accomplish good image quality. Therefore, artificial limitations will influence the ability of the system to actually achieve the optimal techniques in the trajectories. Incorporating a separate loop can allow the closed loop dose control to override the desired trajectory values. The override can occur whenever the control is limited in its ability to satisfy dose requirements. This may happen due to system power and external regulation entrance dose limits and improper positioning by the operator.

Figure 1:
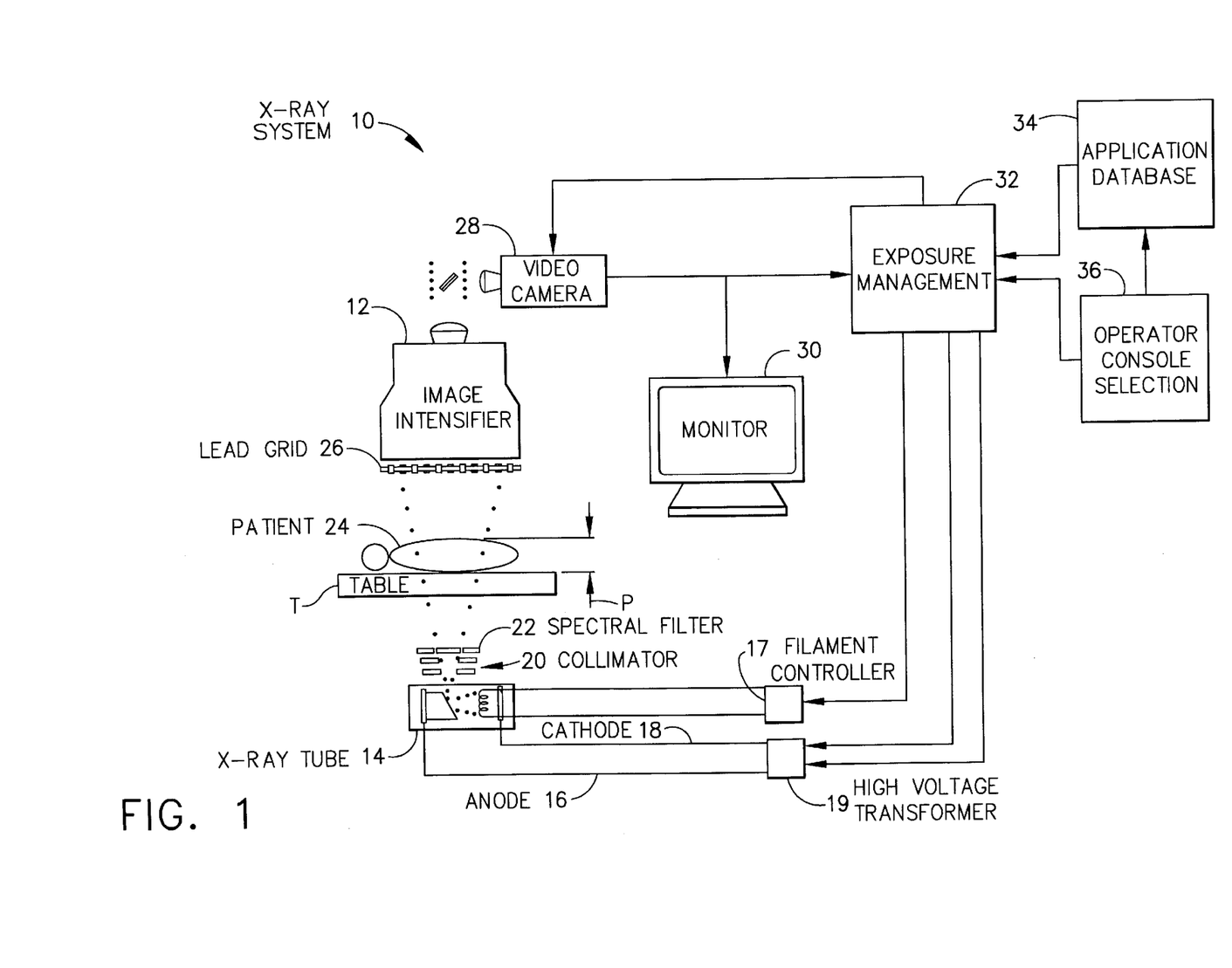
FIG. 1 is a block diagram of an x-ray system incorporating the present invention, having both fluoroscopy and radioscopy capabilities.

Referring now to the drawings, FIG. 1 illustrates an x-ray system 10 which has both fluoroscopy and radioscopy capabilities. The system 10 illustrated uses an analog detector, i.e., image intensifier 12. However, the same model described herein can be applied to a system with a digital detector.

In FIG. 1, the image intensifier 12 receives x-rays produced by x-ray tube 14. The tube 14 has an associated anode 16 and cathode 18 structure. Also associated are a filament controller 17, and high voltage transformer 19. Collimator 20 collimates the x-rays. The x-rays may be filtered by spectral filter 22 before being transmitted through the object under study, such as human patient 24. Finally, the x-rays are received by image intensifier 12 after passing through a lead anti-scatter grid 26. The image is transmitted through camera 28 and output to monitor 30. Various control and selection features are associated with exposure management block 32, application database 34 and operator console selection 36.

Optimal image quality for fluoroscopy or radioscopy is achieved. Desired levels of certain control variables for x-ray generation is based on present patient absorption characteristics. To automate this process, it is desirable to be able to predict patient absorption during fluoroscopy. Typically, the region of interest during a procedure is confined in certain body area where absorption characteristics stay constant. Cross-sectional thickness, a good representative of patient absorption characteristics, and its prediction is used in automating x-ray technique selection process.

For real-time monitoring and reporting purposes, it is often desirable to predict patient radiation exposure or air kerma. A software-based radiation exposure predictor is a less expensive and less system invasive alternative to a hardware-based dose sensor. A less system invasive alternative is one that is not in the x-ray path.

Patient thickness P at some cross section is represented by an equivalent thickness of acrylic glass that produces the same x-ray attenuation. Patient skin dose is represented by the entrance dose to the table T on which the patient is lying. Clearly, several models are required to define the relationship between acrylic and real body absorption. Such models depend on which part of the body is being modeled. Also, the spectral filter 22 is made of slices of aluminum, copper or any other similar material.

Figure 2:
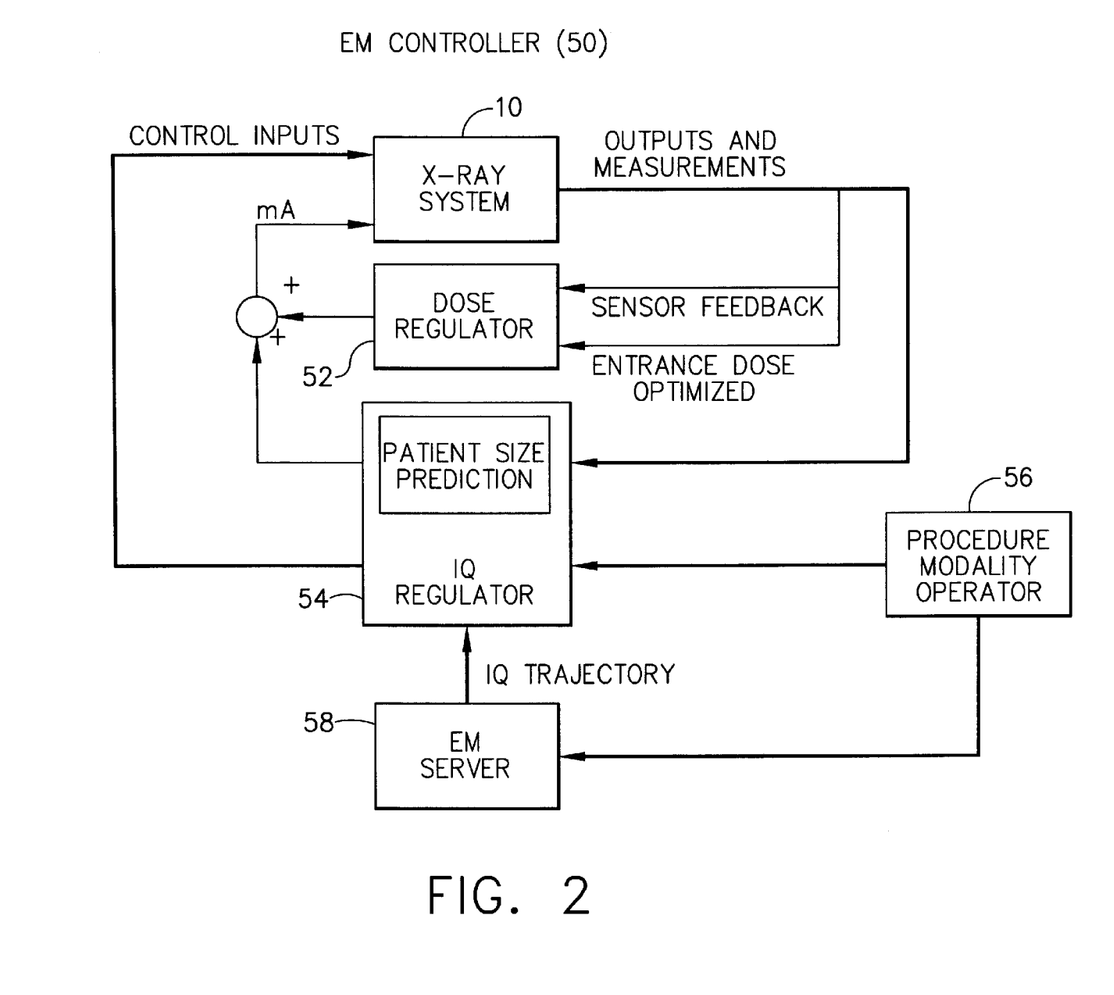
FIG. 2 is a flowchart block diagram illustrating functions of the exposure management and control system of the present invention.

The exposure management and controller comprises several functions, each of which provide improved brightness control and technique selection automation. Block diagram 50 of FIG. 2 illustrates the relationship between each of these functions and the system as a whole. In a preferred embodiment, the exposure management and controller comprises both real time operations and background functions. The real time functions include two regulator loops, to dose regulator 52 and image quality regulator 54. These two loops replace the single automatic brightness control loop of prior art brightness controls.

The detector entrance dose regulator 52 is the control loop responsible for instantaneous dose or brightness control. A single parameter, mA, will control dose or brightness independently from the constraint of optimum image quality. Dose or brightness error alone will drive this loop. Transient response is the primary responsibility of the brightness regulator. Complementarily, the static operation is determined through the image quality regulator loop 54.

Image quality regulator 54 provides desired image quality performance by specifying x-ray techniques at appropriate values for the view being acquired. To achieve this, knowledge of the exam type and patient size is required. Procedure information, system selections and patient size are also used to set proper technique. This information is used with the active image quality trajectory (i.e., technique data tables) appropriate for the particular exam. The optimal imaging technique is chosen from the loaded image quality trajectory as a function of relative patient size. The size is calculated within the image quality regulator 54. The calculation uses data obtained during an acquisition by a neural net trained to the x-ray spectra of the system. This system enables the appropriate x-ray technique to be established and maintained as the image is panned around the patient. Dynamic control of contrast, patient dose, image receptor exposure or exposure rate, image brightness, motion un-sharpness can be achieved. This is accomplished by modifying the image quality trajectory within the image control regulator control parameters.

The image quality trajectories are key in providing optimal image quality. The image quality trajectories can be generated a priori and/or real-time. These trajectories are managed in the exposure management server 58. The use of the trajectories in the image quality regulator, then, provide the optimal image quality. System selections and medical procedure data from procedure modality operator 56 can be inputted into exposure management server 58. When inputted, the correct techniques or trajectories for each parameter can be determined as a function of patient size. In this manner, many different imaging requirements may be selected and controlled. For example, low dose (for neurological applications) vs. high contrast (interventional studies) modes could be selected. The outputted trajectory from the exposure management server 58 procedurally controls the response paths of the image quality regulator. This is based on calculations through the image quality trajectories. The result is image quality and brightness/dose control performance consistent with application needs and user preferences.

Figure 3:
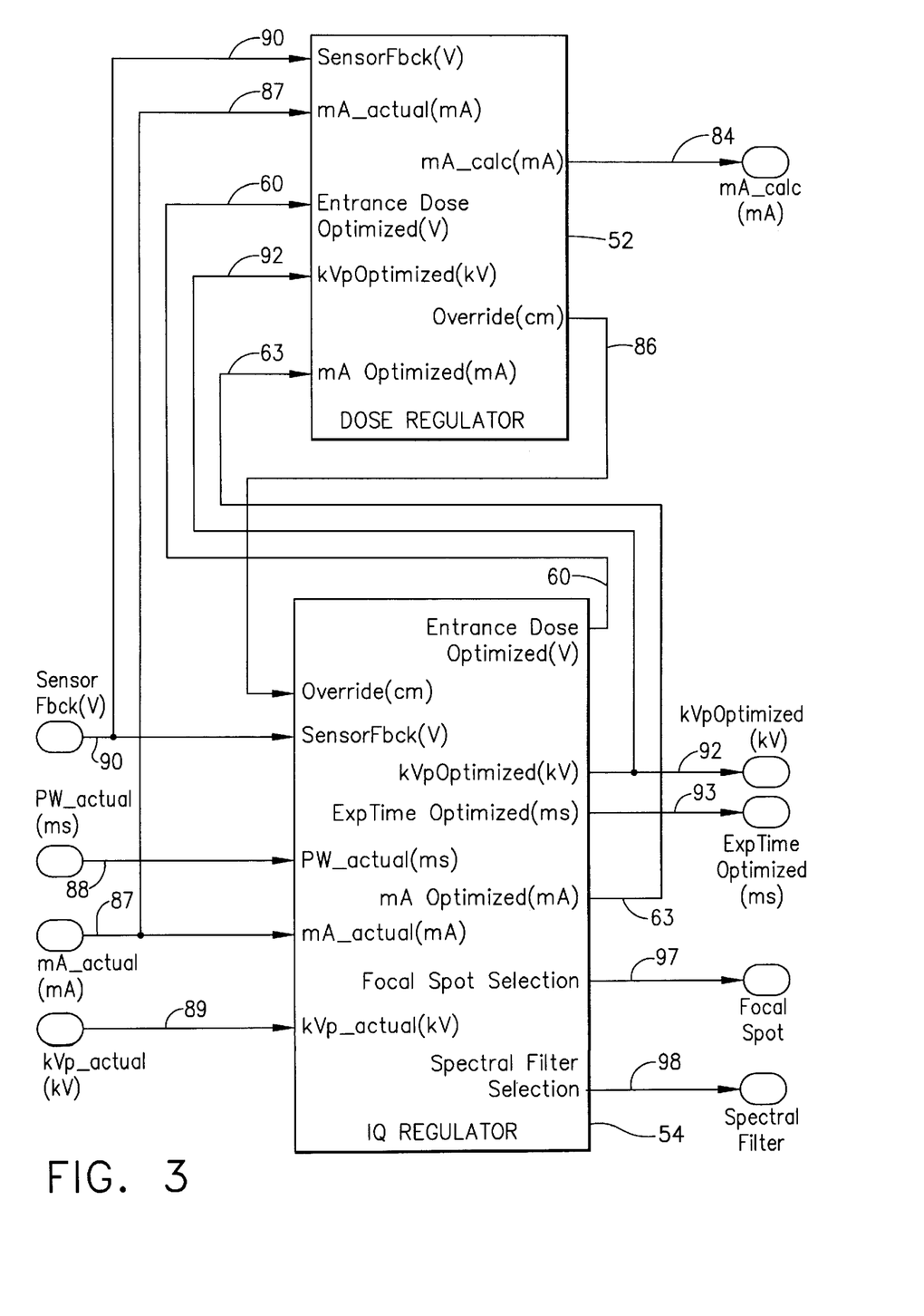
FIG. 3 is a schematic block diagram of a brightness regulator function of FIG. 2.

FIG. 3 illustrates the relationship of the dose and image quality regulators to each other and the x-ray system. This is illustrated through signal inputs and outputs. The dose regulator 52 receives two inputs from the system in terms of feedback signals. These represent the resultant entrance exposure value, sensor feedback 90, and the mA that caused that exposure, mA actual 88. Three control reference signals, entrance dose reference optimized 60, kVp optimized 92 and mA optimized 63 are input. The image quality regulator inputs these signals. These signals are utilized in functions that control output ma_calc 84 along with feedback inputs 88 and 90.

The image quality regulator 54 of FIG. 3 develops override signal 86. Signal 86 is sent from the dose regulator 52 along with the four actual technique input signals. The our signals include sensor feedback 90, mA actual 88, mA actual 87, and kVp actual 89. These inputs provide the x-ray technique information for patient prediction to function. Four outputs from the image quality regulator 54 represent the optimized x-ray technique. These include entrance dose reference optimized 60, kVp optimized 92, Exp Time optimized 93, and mA optimized 63.

Figure 4:
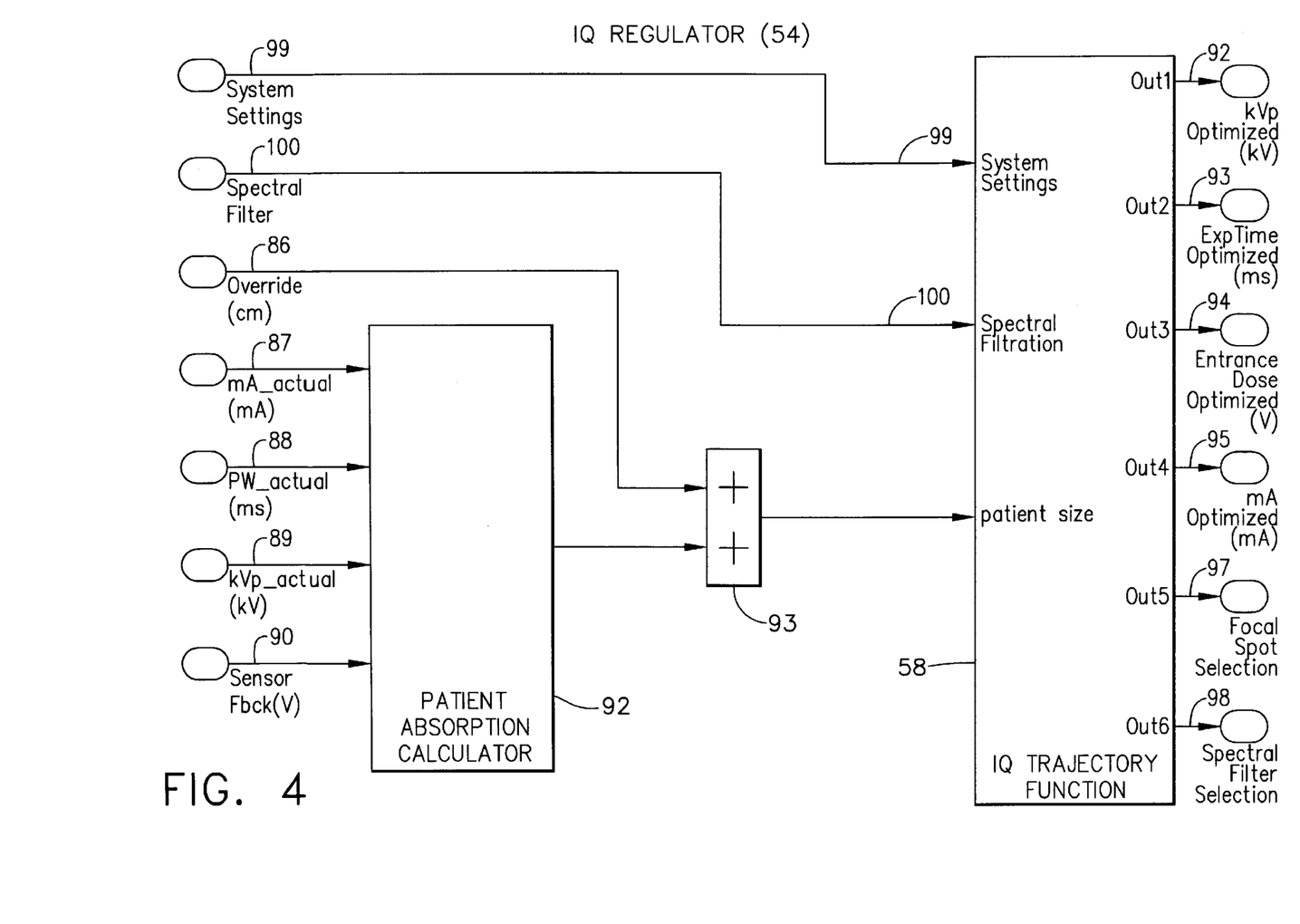
FIG. 4 is a schematic block diagram of an override function relating to an image quality feature in FIG. 2.

The IQ regulator, illustrated in FIG. 4, provides an appropriate technique and desired receptor exposure rate to produce proper IQ properties. The technique includes kVp, pulse width, focal spot, x-ray beam spectral quality. The image quality properties include contrast, signal/noise ratio and/or motion stoppage. These are produced to be consistent with the clinical requirements and at a patient skin dose consistent with good practices. These requirements change with procedure. Therefore, the image quality regulator is programmable to adjust to different clinical needs. To accomplish these goals, image quality regulator 54 is comprised of two major elements. The two major elements include a patient absorption (relative size) calculator 92 and a programmable technique trajectory 58. Both of these elements are driven by patient absorption.

According to x-ray generation principle, knowing certain parameters allows determination of other parameters. The known parameters include control signals (kVp actual 90, mA actual 87). The known signals also include system setting 99 (for example fov, detail, sid, sod, application procedure, etc.). The known signals further include x-ray beam spectral quality (spectral filtration 100), and patient information (patient thickness 93). These known parameters allow the sensor feedback 90 signal (absorbed energy in image receptor) to be uniquely determined. These known signals also allow patient skin dose and receptor entrance dose to be uniquely determined.

However, the problem solved by the present invention is as follows. Control signals (kV, mA), system setup (fov, detail, sid, sod, application procedure, etc.), x-ray beam spectral quality (spectral filtration information: Al thickness, Cu thickness, etc.) and certain measurements (sensor feedback signal, receptor dose at reference brightness) are known. Then principles of the present invention can be applied to find corresponding patient thickness and patient skin dose. This, clearly, is a non-causal relationship.

A neural network (patient absorption calculator 92) is used to map this complex input/output relationship. The parameters of a neural network are the weights that represent the strengths of the interconnections between nodes (or neurons), and the thresholds of some of the nodes. A neural net can have a feed-forward structure, that has just forward connections, or recurrent structures with reflexive, lateral, and backward connection weights as well.

A neural network operates in two stages, including a learning (or training) phase and an operation phase. The purpose of the learning phase is to determine the appropriate parameters that will enable the network to function properly in the operation phase. A training algorithm is used in the learning phase. A neural network can be trained to perform complex functions, especially non causal-effect relationships.

The topology of a neural network defines the number of parameters to be determined. In effect, the learning phase is a nonlinear hypercurve fitting in hyperspace. This phase is then an optimization problem where the objective function to be minimized is the error between the desired output and the neural net output. Search directions are computed that realize the minimum of this error function. The dimension of this search space is equal to the number of neural network parameters to be estimated, and each axis of this space is one of those parameters. The most common optimization algorithm used during this phase is 'backpropagation', which is an approximation to the well-known 'steepest descent' method. At first, a search direction is computed which will result in the steepest descent of the error function. Then, it computes a suitable step size along that direction. This process is repeated iteratively until the error function becomes, basically, zero. In this learning phase, a data set that includes input and corresponding desired output is to be available. During this phase, just part of this data is used in the optimization process mentioned above.

Final neural network parameters are obtained at the end of the learning phase. The next step involves feeding this trained neural network with data subsets is fed to of the original data set, and these are input (without their corresponding desired output) during the training phase. Comparing the "actual output" of the neural network (due to the input set) then uses a validity metric with the "desired output". Such metrics are error sum squares, error sum square average square root, or others. If the estimation results are satisfactory, then the net is ready to be used in an operating environment such as on-line implementation. If the net results are not satisfactory, then certain parameters, such as data set, neural network structure, or optimization algorithm need to be reexamined.

The prediction of patient thickness and patient dose level are based on the information of kVp and average mA. It is also based on a dose sample that represents detector entrance dose. It is also based on an entrance dose that is calibrated against reference level of brightness signal. X-ray beam spectral quality (HVL and on the information of spectral filters, including copper filter thickness and aluminum filter thickness), is also used. Finally, X-ray tube gain (mR/mAs) is used. Each input variable is normalized before being sent to the model. Each output variable needs to be "reverse-normalized" to get back to its true value. This neural net model is first trained on a subset of a big data set that is either generated by a physics-based model or collected in a lab environment. After the training session is successfully completed, the neural network is then tested on the remaining subset of the data set.

Referring now to FIG. 4, in order to change from one technique to another as the patient absorption changes with panning, a controller may be employed to provide a smooth transition between operating points. Inputs such as mA 87, kVp 89, system settings at block 99 and sensor feedback (SensorFdbk) 90 are provided to a relative absorption calculator 92. The output of the absorption calculator 92 is used to determine the optimal technique from trajectory function 58, in a preferred embodiment. Several implementations are possible for function 58. Look up tables have been chosen in order to reduce computation time needed for a full optimization search which would otherwise be required.

In FIG. 4, the override signal 86 from the dose loop is also summed at this point. When the dose loop is not in saturation, the override input is null (zero) providing no contribution to the calculated absorption value. If the dose loop reaches a predetermined limit, the override signal will rise or fall, creating an artificial absorption value greater or less than actual. This action will continue until the dose loop is again out of limit.

Once an absorption number is determined at the output of the summer 93, it is applied to the trajectory function 58 where the appropriate techniques for the clinical imaging needs for this particular patient size can be determined. In a preferred embodiment, a group of look up tables are created which contain the optimized techniques, one table for each clinical need.

Each of the techniques, kVp optimized 92, Exp Time optimized 93, entrance dose optimized 94, mA optimized 95, focal spot 97 and spectral filter selection 98 are applied to the system high voltage generator for the next exposure in the sequence. These procedures are repeated as often as required during an exposure sequence to maintain the desired image quality at the users viewing monitor.

Figure 5:
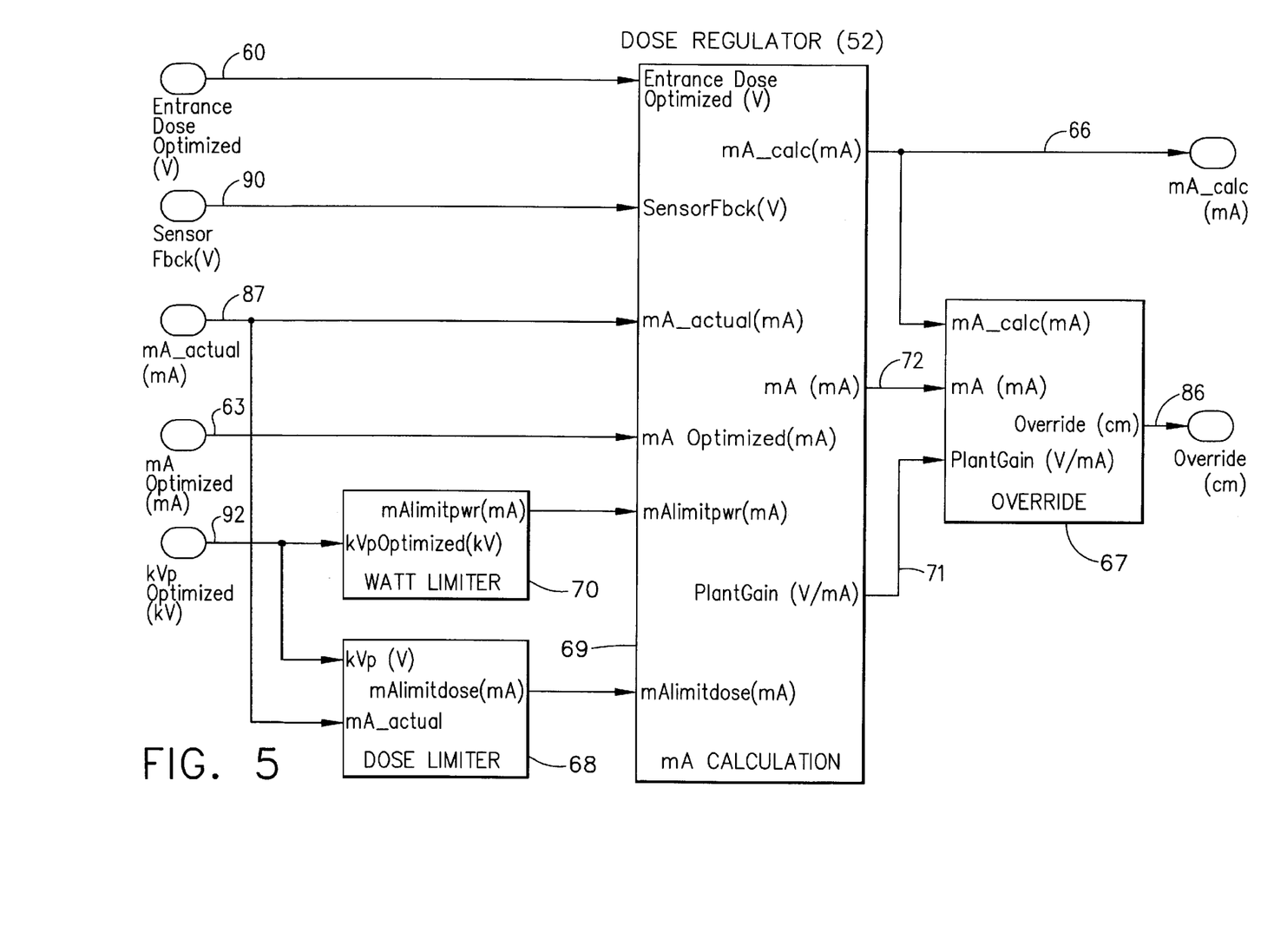
FIG. 5 is a schematic block diagram of the image quality regulator function of FIG. 2.

FIG. 5 provides a breakdown of the various functions contained in the dose regulator 52, from FIG. 3. There are two limiter functions, watt limiter 70 and dose limiter 68, which calculate the peak mA at which each limit would be reached. This is based on operating kVp and present source to skin distance. The watt limiter 70 is used to limit the power, asked for by the regulator, to the limits imposed by the system components such as high voltage generator 19 or X-ray tube 17 limitations. Each result of these limit calculations is compared to the mA result from the mA calculation 69 and the lowest value is output as mA calculation 66.

The mA calculation compares the entrance dose optimized 60 to the sensor feedback 90 and determines the appropriate peak mA needed. That is, needed to make the sensor feedback 90 equal the entrance dose optimized 60. This value is output, once compared with the limit values, and used to produce the next exposure. The mA actual 87 input is used to control the gain of the mA calculator 69 so that the response is stable in closed loop operation. The output, plant gain 71, represents the gain value used by the mA calculation 69. The mA needed output 72 provides the mA required to satisfy the entrance dose optimized 60. When not in limit, the mA calculated 66 and mA needed 72 agree in value. When the mA calculated 66 is limited as described earlier, the difference between mA needed and mA calculated indicates the amount of increase needed to satisfy the entrance dose optimized 60.

Whenever either dose limiter 68 or watt limiter 70 limits the mA calculation, optimal entrance dose 60 cannot be realized. This could occur for several reasons. The operation of the gantry at extreme SIDs, which would create a need for more mA than can be delivered would result in the watt limiter 70 clamping the mA calc output. If the skin dose limit is reached, the dose limiter 68 would clamp the mA calc output from producing more emission than allowed by this limit. In order to allow a non-optimal technique to bring the system to a satisfactory operating point, an override function 67 is employed. The preferred implementation uses look up tables, trajectories 58. Therefore, a means to increase the techniques provided by the table for the actual patient size prediction is needed. The override 67 function provides an additional patient size input, based on the mA required to satisfy the entrance dose optimized.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An x-ray system technique control system comprising:
   an image quality regulator; and
   a dose error regulator, independent of the image quality regulator, for cooperating with the image quality regulator to provide x-ray technique optimization.

2. A control system as claimed in claim 1 wherein the image quality regulator comprises;
   a means for determining x-ray techniques;
   a means for determining receptor dose per image;
   a means for calculating patient absorption using the x-ray techniques and receptor dose per image determinations;
   a means for using the patient absorption calculation and predetermined clinical imaging requirements to determine an optimal technique; and
   a means for adjusting the optimal technique up or down when the dose error regulator is in limit.

3. A control system as claimed in claim 2 wherein the patient size is calculated through a neural net trained with real or modeled technique and entrance dose data.

4. A control system as claimed in claim 2 wherein the optimal technique is determined through a look up table containing optimal techniques determined a-priori and loaded into the image quality regulator based on system selections.

5. A control system as claimed in claim 2 wherein the optimal technique is determined through real time technique optimization using a model based optimization engine.

6. A control system as claimed in claim 2 wherein the optimal technique is determined by creating a real time look up table containing optimized techniques at selection time utilizing a model based optimization engine.

7. A control system as claimed in claim 1 wherein the dose error regulator comprises:
   a means for determining entrance dose error from a comparison of measured entrance dose and a reference dose;
   a means for limiting power output to protect limitations of the x-ray system;
   a means for preventing exposure to a patient from exceeding regulatory limits or any desired level; and
   a means for indicating a non-optimal control setting resulting from limit conditions.

8. A control system as claimed in claim 7 wherein the reference dose comprises an optimized reference dose.

9. A control system as claimed in claim 7 further comprising a means for correcting the entrance dose.

10. A control system as claimed in claim 9 wherein the means for correcting the entrance dose comprises means for controlling x-ray tube emission current.

11. A control system as claimed in claim 9 wherein the means for correcting the entrance dose comprises means for controlling x-ray tube potential.

12. A method of x-ray system image quality control selection comprising the steps of:

provaiding an image quality regulator;

providing a dose error regulator; and inducing the image quality regulator to cooperate with the dose error regulator to optimize image quality control selection.

13. A method as claimed in claim 12 wherein the step of inducing cooperation comprises the steps of:

defining a clinical application;

defining key image quality attributes for the clinical application;

determining optimal control parameters as a function of patient absorption, to generate an optimization;

providing a computer model to numerically perform the optimization with a computer model of the x-ray system;

calculating attenuation factors based on previous x-ray exposures; and optimizing image quality control selection using the computer model and the attenuation factors.

14. A method as claimed in claim 13 wherein the image quality regulator utilizes x-ray tube emission as an independent brightness control while allowing automatic setting of x-ray tube peak voltage, exposure time and video gain to independently set contrast, signal-to-noise ratio and motion stopping requirements for the clinical application.

15. A method as claimed in claim 13 further comprising the step of using a first exposure sequence to determine a proper technique for subsequent exposure sequences, regardless of changes initiated by an operator with respect to field of view, mode selections and accompanying entrance dose change or frame rate changes.

16. A method as claimed in claim 13 further comprising the steps of:

calculating skin dose delivered to a patient; and controlling the skin dose needed for optimal visualization by adaptive control based on clinical application requirements.

17. A method as claimed in claim 13 further comprising the step of using a real time model to predict both cross-sectional absorption and skin dose of a patient for all x-ray acquisition modes.

18. A method as claimed in claim 13 further comprising the step of using a neural network trained to model complex x-ray spectra input/output relationships.

* * * * *